(12) United States Patent
Fisher et al.

(10) Patent No.: US 10,765,411 B2
(45) Date of Patent: Sep. 8, 2020

(54) OSCILLATING SYRINGE SYSTEM

(71) Applicant: John Steele Fisher, Belleair, FL (US)

(72) Inventors: John Steele Fisher, Belleair, FL (US); Wayne A. Noda, Mission Viejo, CA (US); Daniel Hyman, Foothill Ranch, CA (US); Jon Jacobson, Irvine, CA (US)

(73) Assignee: John Steele Fisher, Belleair, FL (US)

( * ) Notice: Subject to any disclaimer, the term of this patent is extended or adjusted under 35 U.S.C. 154(b) by 0 days.

(21) Appl. No.: 16/411,091

(22) Filed: May 13, 2019

(65) Prior Publication Data

US 2020/0100778 A1 Apr. 2, 2020

Related U.S. Application Data (60) Provisional application No. 62/756,374, filed on Nov. 6, 2018, provisional application No. 62/738,849, filed on Sep. 28, 2018.

(51) Int. Cl.
*A61B 10/02* (2006.01)
*A61B 17/34* (2006.01)
*A61B 17/32* (2006.01)

(52) U.S. Cl.
CPC ...... *A61B 10/0283* (2013.01); *A61B 17/3476* (2013.01); *A61B 2017/32007* (2017.08)

(58) Field of Classification Search
CPC ............ A61B 10/0283; A61B 17/3476; A61B 2017/32007
See application file for complete search history.

(56) References Cited

U.S. PATENT DOCUMENTS

| 3,811,442 A * | 5/1974 | Maroth ................. A61M 5/20 604/188 |
| 5,651,372 A * | 7/1997 | Caillouette ........ A61B 10/0283 600/567 |
| 6,702,761 B1 | 3/2004 | Damadian et al. |
| 7,828,748 B2 | 11/2010 | Hibner |
| 2007/0149893 A1 | 6/2007 | Heske et al. |
| 2015/0283334 A1 | 10/2015 | Marx et al. |

FOREIGN PATENT DOCUMENTS

WO    2009058436 A1    5/2009

OTHER PUBLICATIONS

International Search Report and Written Opinion from the counterpart PCT Application PCT/US2019/053531 dated Jan. 10, 2020.

* cited by examiner

*Primary Examiner* — Patrick Fernandes
(74) *Attorney, Agent, or Firm* — John L. Rogitz (57) ABSTRACT

A syringe is coupled to a biopsy needle through a coupling structure that includes a motor-driven element such as a gear to rotate the needle. The motor can oscillate back and forth to cause the needle to oscillate. Structures are described to permit one-handed operation of the device and automatic motor activation based on attaining a desired plunger position.

14 Claims, 13 Drawing Sheets

FIG. 15

OSCILLATING SYRINGE SYSTEM

FIELD

The application relates generally to syringe systems, and more particularly to biopsy syringe systems with oscillating needles.

BACKGROUND

It may be necessary to extract tissue from a patient for analysis to support diagnosis. For example, it may be necessary to extract tissue for "cytological" or cell harvest, as well as cores of tissue for breast biopsies, to ascertain the existence of disorders of the tissue.

Tissue extraction may be done by inserting a needle into the patient to withdraw tissue into the needle, which is then removed from patient for dispensing the tissue onto analysis equipment.

SUMMARY

In the present assignee's co-pending U.S. patent application Ser. No. 16/013,522, incorporated herein by reference, a motorized convenient tissue extraction device is disclosed that conveniently avoids multiple needle insertions in the patient to obtain sufficient tissue for analysis while harvesting sufficient tissue for analysis.

Present principles are directed to oscillating the motorized needle to prevent the needle from being wrapped in connective fibrous tissues. Present principles are also directed to techniques for facilitating one-handed operation of the device to leave the other hand free for, e.g., positioning an ultrasound probe for imaging, while activating the motor automatically when the correct plunger position is attained.

Accordingly, in an aspect, a device includes an elongated needle having a cutting tip and a hollow interior. A syringe is coupled to the needle for rotation of the needle relative to the syringe, with an evacuatable tissue chamber being established at least in part by the hollow interior of the needle. A motor is coupled to the needle to oscillate the needle back and forth while the tissue chamber is evacuated, and the needle is disposed in tissue to facilitate drawing cells from the tissue into the tissue chamber.

In embodiments, the syringe includes a barrel and a plunger slidably disposed in the barrel and movable to evacuate the tissue chamber. The device can further include a plunger activation assembly that in turn includes a receptacle configured for closely receiving a proximal flange of the plunger, and opposed arms extending distally away from the receptacle. At least one of the arms includes an inclined ramp that abuts a motor activation switch in a first plunger position to activate the motor and that does not abut the motor activation switch in a second plunger position to deactivate the motor. In this embodiment, the plunger activation assembly may include a thumb ring extending proximally away from the receptacle. Also, a housing can support the barrel and at least one finger ring can extend transversely away from the barrel. If desired, at least one of the arms may be formed with at least one notch, and a detent arm may extend generally parallel to the plunger and may include a detent adjacent a free end of the detent arm. The detent arm may be biased to a first position, in which the detent engages the notch, and may be movable to a second position, in which the detent does not engage the notch. The detent can be movable to the second position by a detent button.

In other embodiments, the syringe can include a barrel and a plunger slidably disposed in the barrel and movable to evacuate the tissue chamber, and the device can further include a housing supporting the barrel, and a linkage coupled to the housing. The linkage can be movable between a first configuration, in which the linkage is V-shaped and distanced from a motor switch to deactivate the motor, and second configuration, in which the linkage is substantially straight and engages the motor switch to energize the motor. In this embodiment, a plunger activation assembly may include a receptacle configured for closely receiving a proximal flange of the plunger, and at least one plunger activation arm extending distally away from the receptacle, with the linkage being connected to the plunger activation arm.

In another aspect, a device includes a needle, a motor coupled to the needle to rotate the needle, and a switch to energize the motor. The device also includes a barrel in which at least a portion of the needle can reciprocate. A plunger is slidably disposed in the barrel and is movable to evacuate the barrel. A plunger activation assembly receives the plunger and is movable to open and close the switch.

In another aspect, a method includes retracting a syringe plunger proximally relative to a barrel of the syringe to a first proximal position and advancing a needle in fluid communication with the barrel of the syringe into an object to be sampled. The method also includes energizing a motor coupled to the needle to rotate the needle. The method includes reversing a direction of rotation of the motor to reverse a direction of rotation of the needle, retracting the plunger to a second position to cause portions of the object to be sucked into the needle as the needle rotates, and deenergizing the motor. The method includes releasing the plunger from the second position, withdrawing the needle from the object, and advancing the plunger distally to expel the portions of the object from the needle.

In another aspect, a method includes activating a motor to rotate a needle to harvest tissue and deactivating the motor. The activating includes moving a plunger activation assembly coupled to the needle through a syringe to move a switch electrically coupled to the motor.

The details of the present application, both as to its structure and operation, can best be understood in reference to the accompanying drawings, in which like reference numerals refer to like parts, and in which:

DETAILED DESCRIPTION

It is to be understood that principles of constructions and operation set forth in the above-incorporated U.S. patent application apply to the disclosure herein in relevant part taking account of the features set forth herein.

Figure 1:
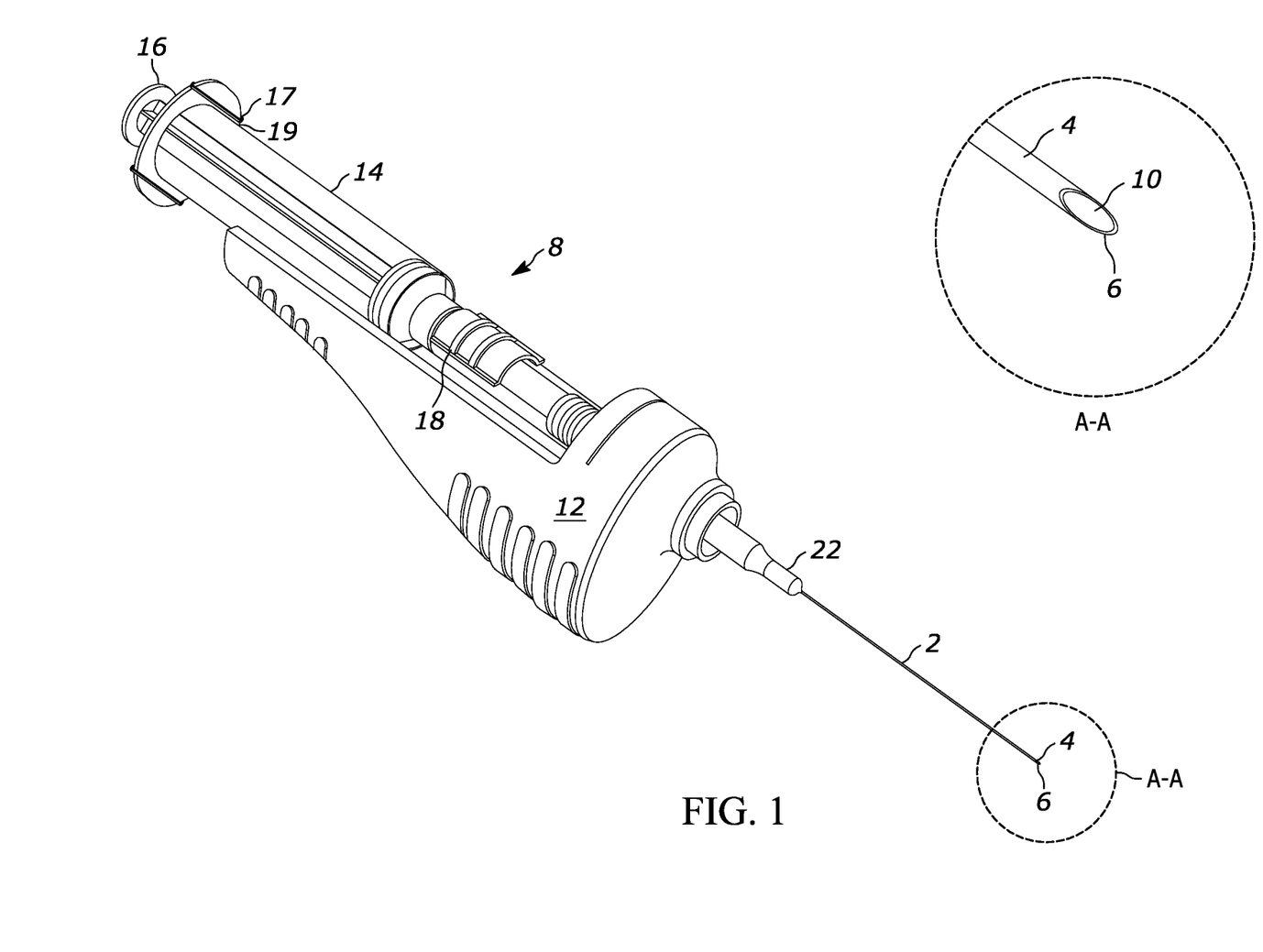
FIG. 1 is a perspective view of a first embodiment of a motor-driven needle assembly.

FIG. 1 shows a device that includes an elongated needle 2. The needle 2 may be a hollow metal hypodermic needle of a size of between 18 to 27 gauge, and more particularly 22-25 gauge with a cutting tip 4 as shown in detail A-A. The cutting tip 4 has a sharp cutting edge 6 that may be beveled as shown to facilitate cutting tissue when the needle 2 is advanced into tissue and rotated.

A syringe 8 is coupled to the needle 2 for rotation of the needle 2 relative to the syringe 8. An evacuatable tissue chamber 10 is established at least in part by the hollow interior of the needle 2. A motor, shown and described further below, is supported in a drive housing 12 and is coupled to the needle 2 to rotate the needle 2 while the tissue chamber 10 is evacuated and the needle 2 is disposed adjacent tissue to facilitate drawing cells from the tissue into the tissue chamber 10.

The syringe 8 typically includes a barrel 14 and a plunger 16 slidably disposed in the barrel 14 and movable to evacuate the tissue chamber 10. A valve such as a slide valve 18 (FIG. 1) or three-way stopcock or other valve structure may optionally be provided to lock vacuum in the tissue chamber 10, although in some embodiments vacuum is established by appropriate manipulation of the syringe without the need for a valve.

Completing the description of FIG. 1, in some embodiments a plunger lock mechanism 17 is engaged with the barrel 14, in this case with a proximal thumb flange 19 of the barrel 14, to engage one or more notches in the plunger 16 to impede advancing the plunger into the barrel (and for that matter to impede withdrawing the plunger out of the barrel). The plunger lock mechanism may include a stiff wire-like structure with a segment riding against the plunger 16 as the plunger is withdrawn proximally until the notch is juxtaposed with the segment to cause the segment to engage the notch under material bias. The plunger 16 can be rotatable in the barrel 14 to disengage the segment from the notch.

Figure 2:
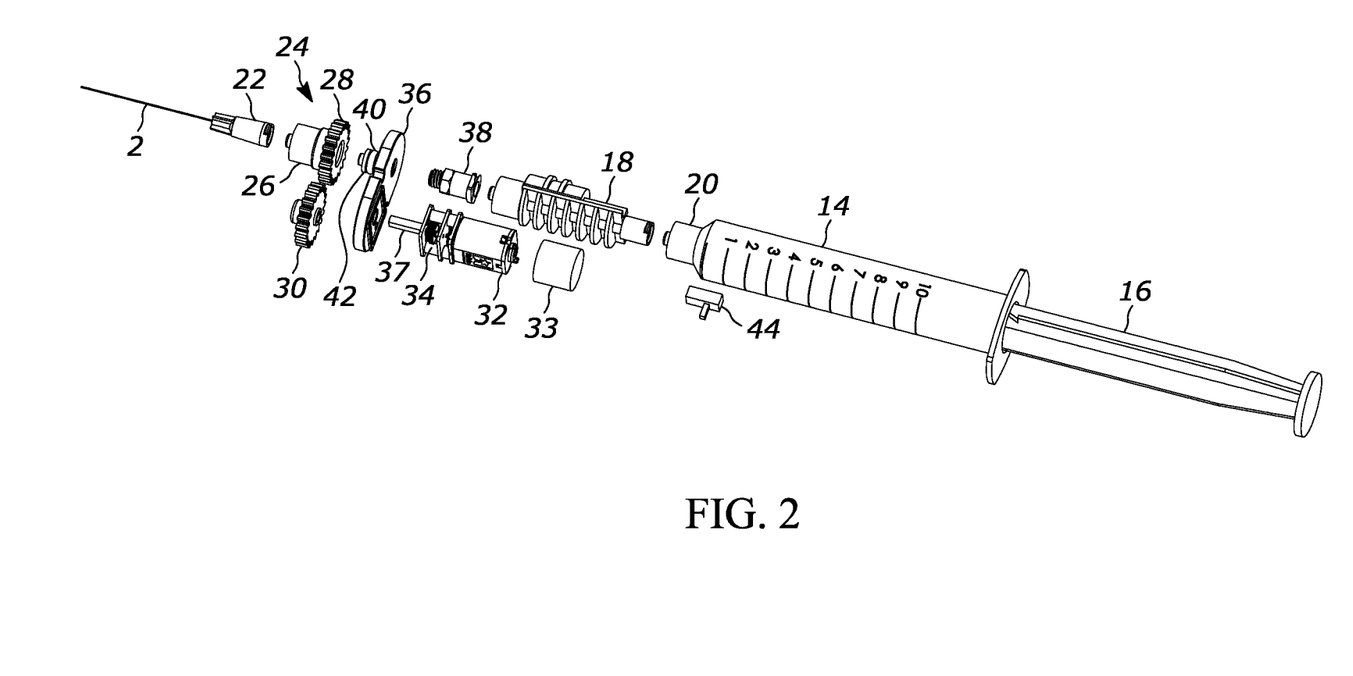
FIG. 2 is an exploded view of the assembly shown in FIG. 1.

In example embodiments, as best shown in FIG. 2 the syringe can include a distal end configured as a connector 20 (the distal end of the syringe 8 is obscured by the drive housing 12 in FIG. 1). The connector 20 may be configured as a Luer fitting. As shown in FIGS. 1 and 2, the needle 2 is engaged with a needle hub 22, and the syringe 8 is coupled to the needle 2 by a coupling that includes at least the needle hub 22 and the connector 20. The needle hub 22 can be established by a hollow Luer fitting such as a female Liter fitting.

As illustrated in FIG. 2 the above-mentioned coupling may include a hollow fitting 24 engaged with the needle hub 22. In the example shown, the hollow fitting 24 includes a body 26 that may be configured as a male Luer fitting and a driven gear 28 circumscribing the body 26 and meshed with a drive gear 30 that is coupled to a small electric dc-powered motor 32 through a reduction gear assembly 34, which reduces rotational speed to be between sixty (60) revolutions per minute (RPM) to three hundred fifty (350) RPM, inclusive (which is therefore the rotational speed of the needle 2). The motor may be a six-volt DC gear motor operating at three VDC and powered by a battery 33 in the motor housing. These specifications are examples only. A Lithium or alkaline or other type of battery may be used, and the motor could operate at other voltages, e.g., 12 VDC operated by a 9 VDC battery or 12VDC battery at, e.g., 330 RPM.

A support assembly 36 may be engaged with the hollow fitting 24 to rotatably support the hollow fitting 24. Note that the output shaft 37 of the gear assembly 34 may extend through a hole of the support assembly 36 to connect to the drive gear 30, with the support assembly 34 radially supporting the output shaft 37 as the shaft spins.

The support assembly 36 is coupled to the connector 20 of the distal end of the syringe 8, if desired via at least one Luer fitting 38 that may be, e.g., glued to the support assembly 36. When the slide valve 18 is included (or another valve such as a stopcock), the Luer fitting 38 is connected to the distal end of the valve 18, which in turn is connected at its proximate end to the connector 20 of the syringe. The valve connectors may be configured as Luer fittings. A continuous fluid passageway is formed from the tip of the needle 2 into the barrel 14 of the syringe by the train of components described above, with the valve 18 being operable to selectively occlude the fluid passageway to draw a vacuum in the system when the plunger is retracted proximally.

The hollow fitting 24 may rotate on a boss 40 of the support assembly 36, against an O-ring 40 that circumscribes the boss 40 to establish a fluid seal between the support assembly 36 and hollow fitting 24 during rotation.

As can be appreciated in reference to FIGS. 1 and 2 and as mentioned above, a fluid passageway for fluid communication is established between the interior of the needle 2 and the syringe 8 by the needle hub 22, rotatable fitting 24, and support assembly 36 such that the syringe 8 is manipulable to evacuate the interior of the needle. The motor 32 that is coupled to the drive gear 30 that in turn is meshed with the driven gear 28 can be energized using a manipulable switch 44 such as a slide switch, toggle switch, moment switch, or other appropriate electrical switch to cause the needle 2 to rotate under influence of the motor 32 while the interior of the needle 2 is evacuated.

FIGS. 3-6 illustrate a first alternative embodiment and FIGS. 7-11 illustrate a second alternative embodiment in which both embodiments provide for one-handed operation of the syringe while energizing the motor to oscillate back and forth upon attaining a desired plunger position. It is to be understood that both embodiments in FIGS. 3-11 may incorporate components from FIGS. 1 and 2, e.g., the distal portions including the needle, etc.

Cross-referencing FIGS. 3-6, a device 200 includes an elongated needle having a cutting tip and a hollow interior such as shown and described above in reference to FIGS. 1 and 2, and a syringe 202 coupled to the needle for rotation of the needle relative to the syringe. An evacuatable tissue chamber is established at least in part by the hollow interior of the needle as described above. The syringe 202 includes an elongated hollow cylindrical barrel 204 and an elongated plunger 206 slidably disposed in the barrel 204 and movable to evacuate the tissue chamber.

A motor 208 (FIG. 5) is coupled to the needle to oscillate the needle back and forth while the tissue chamber is evacuated, and the needle is disposed in tissue to facilitate drawing cells from the tissue into the tissue chamber. Oscillation reduces winding of fibrous connective tissue around the needle, which may otherwise make needle retraction difficult. FIGS. 12-16, described further below, provide example elegant designs that use only discrete components to control the voltage polarity to cause the DC motor to alternate directions, every few revolutions without requiring software.

In FIGS. 3-6, a plunger activation assembly is provided that includes a receptacle 210 oriented generally perpendicular to the long axis defined by the syringe 202 that includes an open top 212 (best shown in FIG. 4) for closely receiving a proximal flange 214 of the plunger 206. Elongated opposed arms 216 extend distally away from the receptacle 210 as shown. A hollow thumb ring 218 extends proximally away from the receptacle 210 for receiving the thumb of an operator of the device. In examples, the receptacle 210, thumb ring 218, and aims 216 are made unitarily with each other from a single piece of molded plastic.

Figure 3:
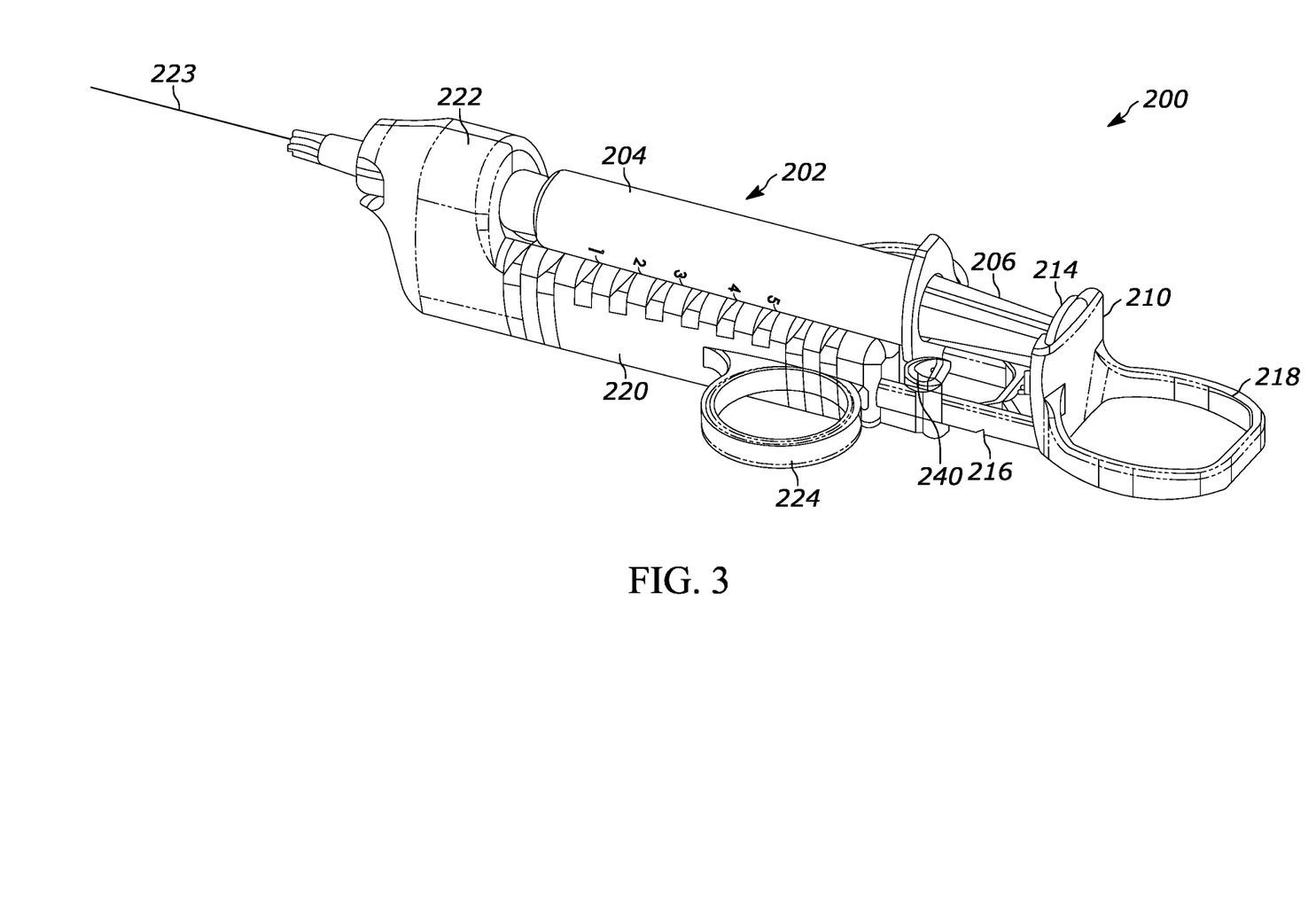
FIG. 3 is a perspective view of an embodiment of a needle assembly in which finger rings permit one-handed plunger control and the motor is activated by motion of a ramp coupled to the plunger riding against a motor switch, omitting the needle and certain other components at the distal end for clarity.

As shown in FIG. 3, the syringe 202 is disposed in a semi-cylindrical trough of a housing 220 with the distal portion of the syringe extending through a gear enclosure 222 of the housing 220 from which a needle 223 extends for rotation of the needle by the motor. The housing 220 contains the below-described motor and motor-related activation components. Left and right finger rings 224 may be provided on the housing and may extend transversely outwardly therefrom to receive fingers of the operator. The thumb ring and finger rings permit single-handed operation of the syringe, which is advantageous because often the other hand manipulates an ultrasound probe for visualization of the needle position in the target tissue.

Figure 4:
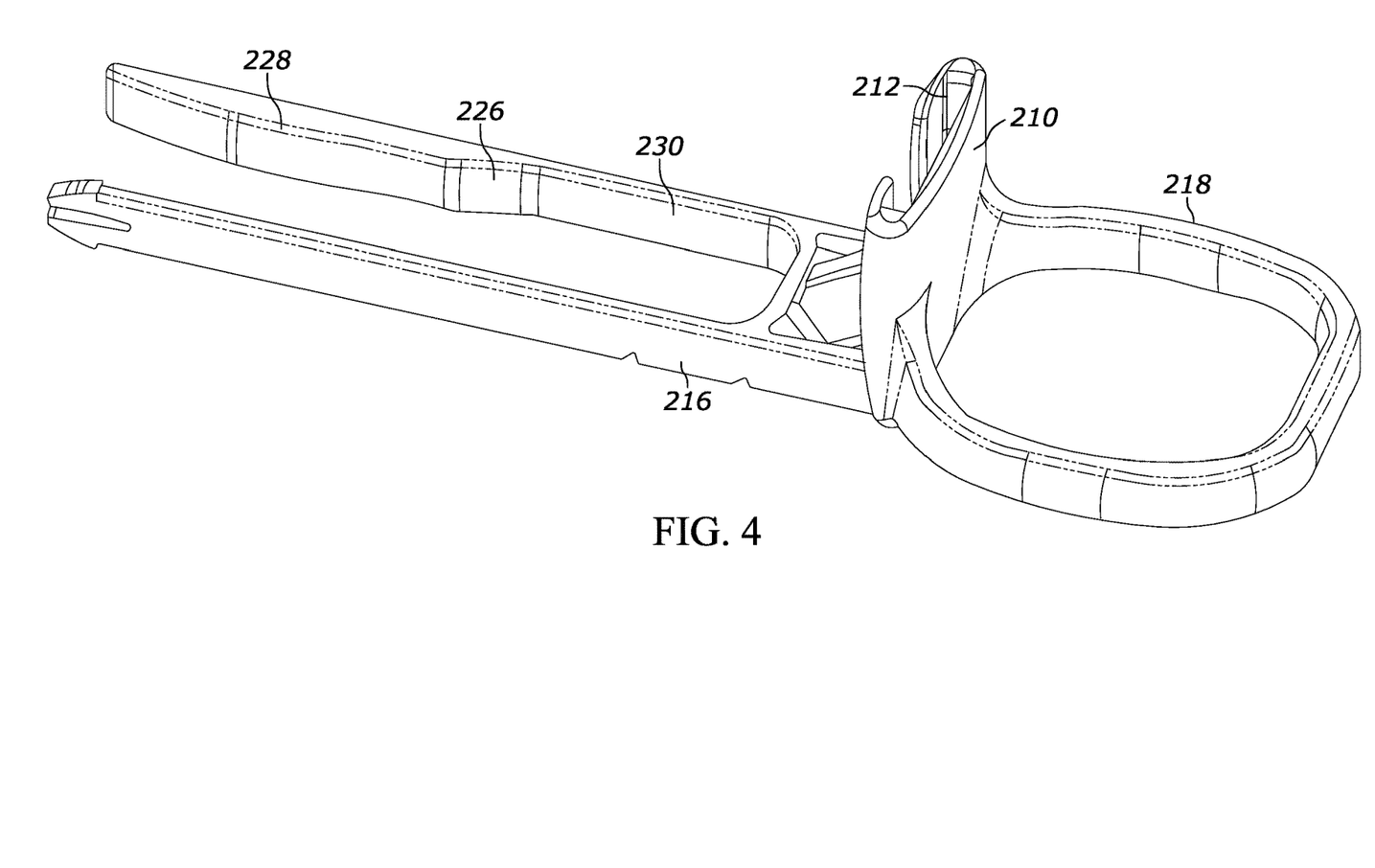
FIG. 4 is a perspective view of the thumb ring and ramp in the embodiment of FIG. 3.
Figure 5:
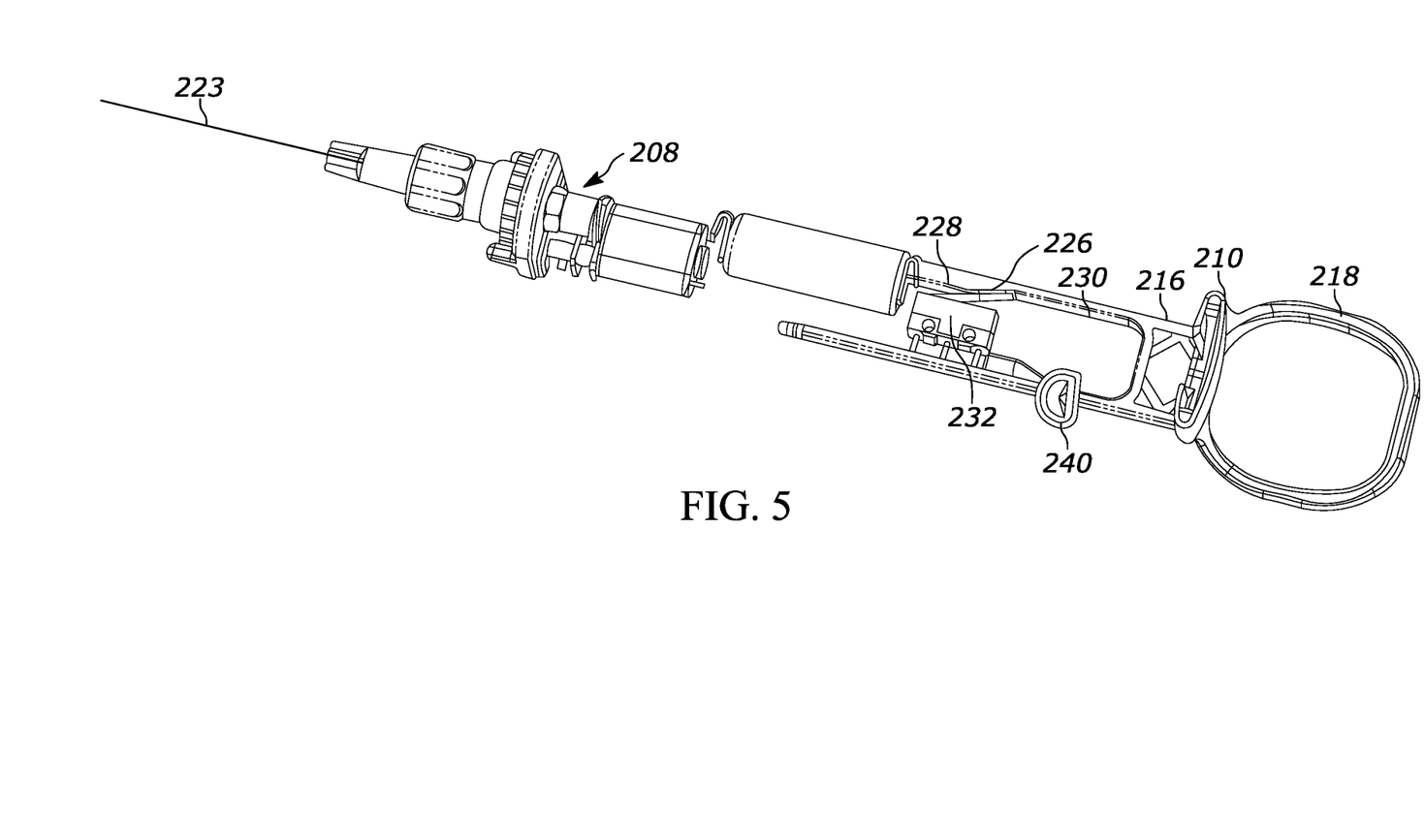
FIG. 5 is a top view of the thumb ring, ramp, and switch of the embodiment of FIG. 3, with the plunger and barrel of the syringe removed for illustration.

As best shown in FIGS. 4 and 5, at least one of the arms 216 includes, on its inner surface, an inclined ramp 226 that extends inwardly from the remainder of the arm 216 to merge with a surface 228 that is generally parallel to and offset inwardly from the proximal segment 230 of the inner surface of the arm 216. The ramp 226 abuts a motor activation switch 232 (FIG. 5) in a first plunger position to activate the motor 208 and does not abut the motor activation switch 232 in a second plunger position to deactivate the motor 208.

With greater particularity, the motor is activated only be on when there is vacuum in the syringe, meaning that the motor is activated by the ramp/switch only in a retracted configuration of the plunger, which causes the ramp 226 to ride against the switch 232 to close the switch 232 and activate the motor. Advantageously the motor is deactivated before any expulsion of captured tissue occurs, i.e., the motor is deactivated when the plunger is advanced fully into the barrel, which causes the ramp 226 to disengage the switch 232 and deenergize the motor.

Figure 6:
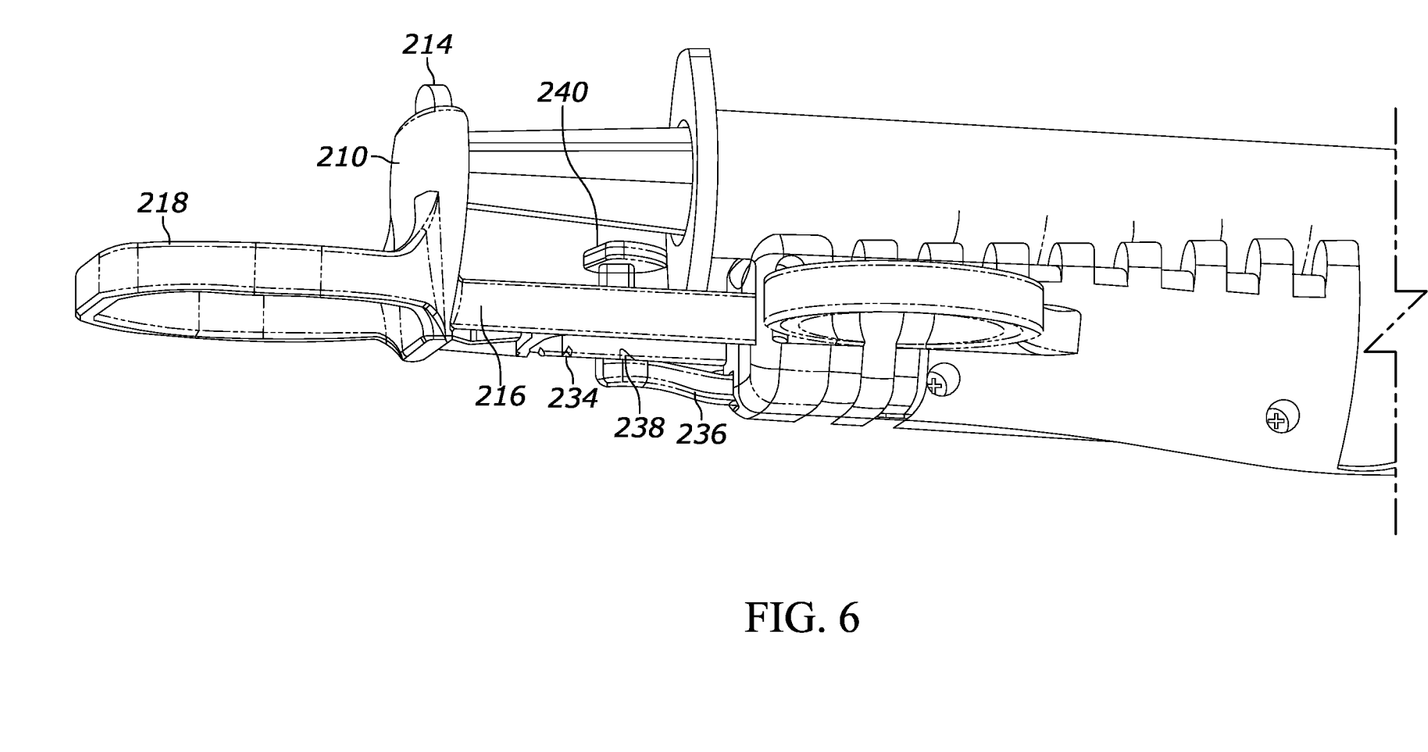
FIG. 6 is a detail perspective view of the proximal portion of the plunger of the embodiment of FIG. 3 showing the detent lock mechanism.

FIG. 6 best shows an additional feature of the device 200 in which one of the arms 216 is fanned with one or more notches 234. A detent arm 236 is attached to and extends proximally away from the housing 220, generally parallel to the arm 216. The proximal end of the detent arm 236 is formed with an inwardly protruding bump or detent 238 with an inclined surface that rides on the plunger control arm 216. The detent arm 236 is biased to a first position, in which the detent 238 engages the notch 234 to lock movement of the plunger in the barrel, and is movable to a second position, in which the detent does not engage the notch to unlock movement of the plunger in the barrel. In the example shown, the detent 238 is movable to the second position by a reciprocable detent button 240 that can be pressed against the detent and/or detent arm to urge the detent 238 out of the notch 234.

At least one of the notches 234 is located at a position in which the plunger is retracted to establish an evacuated space in the barrel 204 of a predetermined volume. In an example, the predetermined volume is two cubic centimeters. One of the other notches 234 may be used for a storage position of the plunger to prevent creepage of the arm 216 (and, hence, plunger 206) during storage, which another of the other notches may be for indicating an end of travel position. The notches 234 and ramped bump or detent 238 may be oriented for one-way action so that the plunger 206 can be retracted without resistance but cannot be advanced distally into the barrel 204 past a notch 234 without depressing the button 240. With particularity, as illustrated in FIG. 6 the ramp surface of the detent 238 increases from a narrow width at the distal end of the detent 238 to a wider width at a proximal wall of the detent 238 that is generally perpendicular to the axis of the syringe.

In operation, after insertion into the target tissue, the plunger 206 can be retracted with the thumb. The internal ramp 228 on the plunger control arm 216 activates the motor switch 232 to energize the motor 208 to rotate the needle and harvest tissue. After harvest, the plunger 206 is advanced partially back into the barrel 204, turning off the motor 208 and continuing travel until the 2 cc notch 234 engages the detent 238. The needle is then removed from the patient and the contents of the syringe 202 can be expelled onto a glass slide by pushing the button 240 to release the detent 238 from the notch 234 and fully advancing the plunger 206 into the barrel 204.

Figure 7:
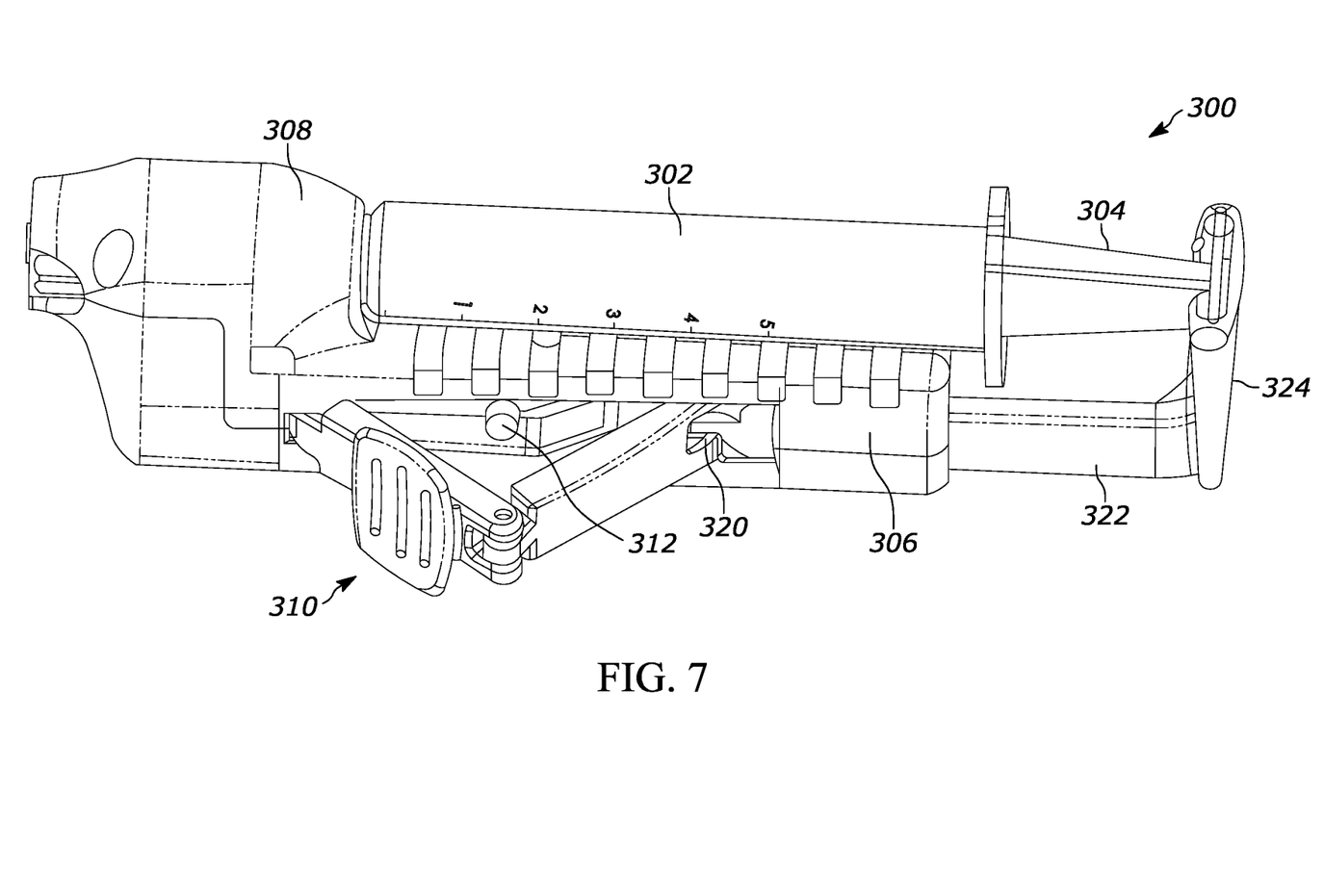
FIG. 7 is a perspective view of an alternate embodiment of a needle assembly in the partially retracted configuration, in which a scissor-type linkage permits one-handed plunger control and the motor is activated by the linkage being manually collapsed against a motor switch in an extended configuration, omitting the needle and certain other components at the distal end for clarity.

Now referring to FIGS. 7-11, a second one-handed operation syringe 300 is shown that also automatically activates and deactivates the motor based on plunger position. The syringe 300 includes a barrel 302 and a plunger 304 slidably disposed in the barrel and movable to evacuate the tissue chamber of the needle (which is removed in FIGS. 7-11 for clarity). As was the case in FIGS. 3-6, the syringe 700 of FIG. 7 is disposed in a semi-cylindrical trough of a housing 306 with the distal portion of the syringe extending through a gear enclosure 308 of the housing 306. The housing 306 contains the below-described motor and motor-related activation components.

Figure 8:
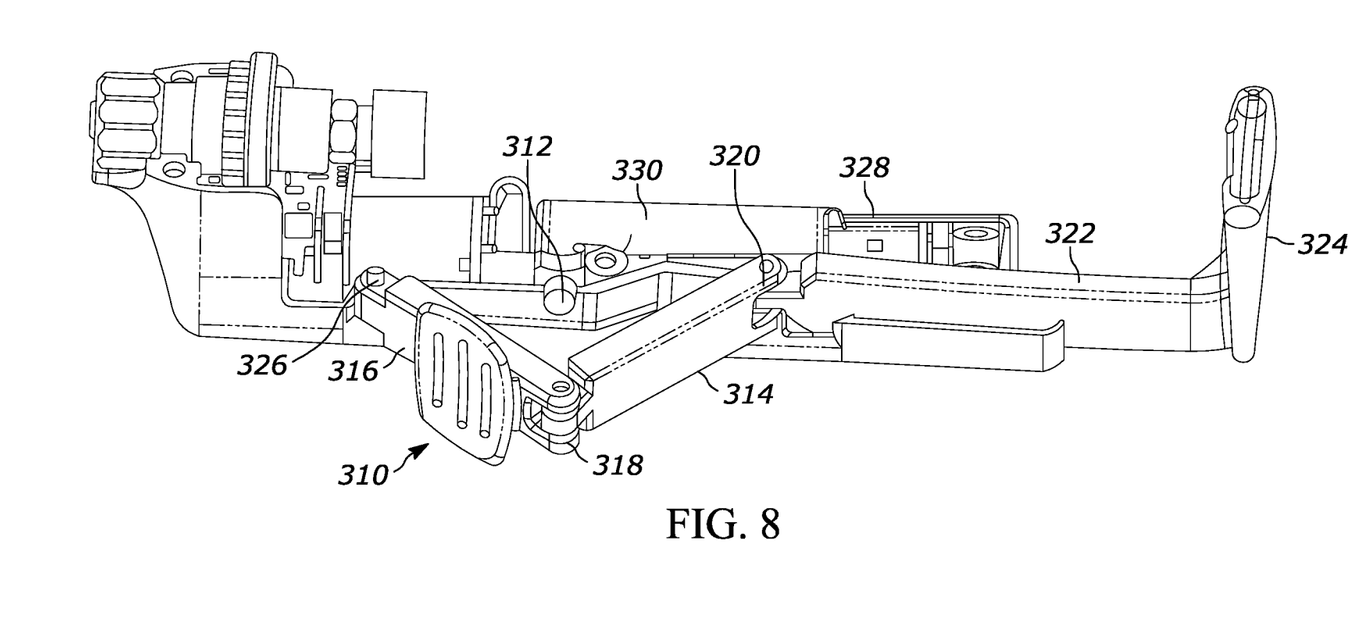
FIG. 8 is a perspective view of the scissor linkage shown in FIG. 7.
Figure 9:
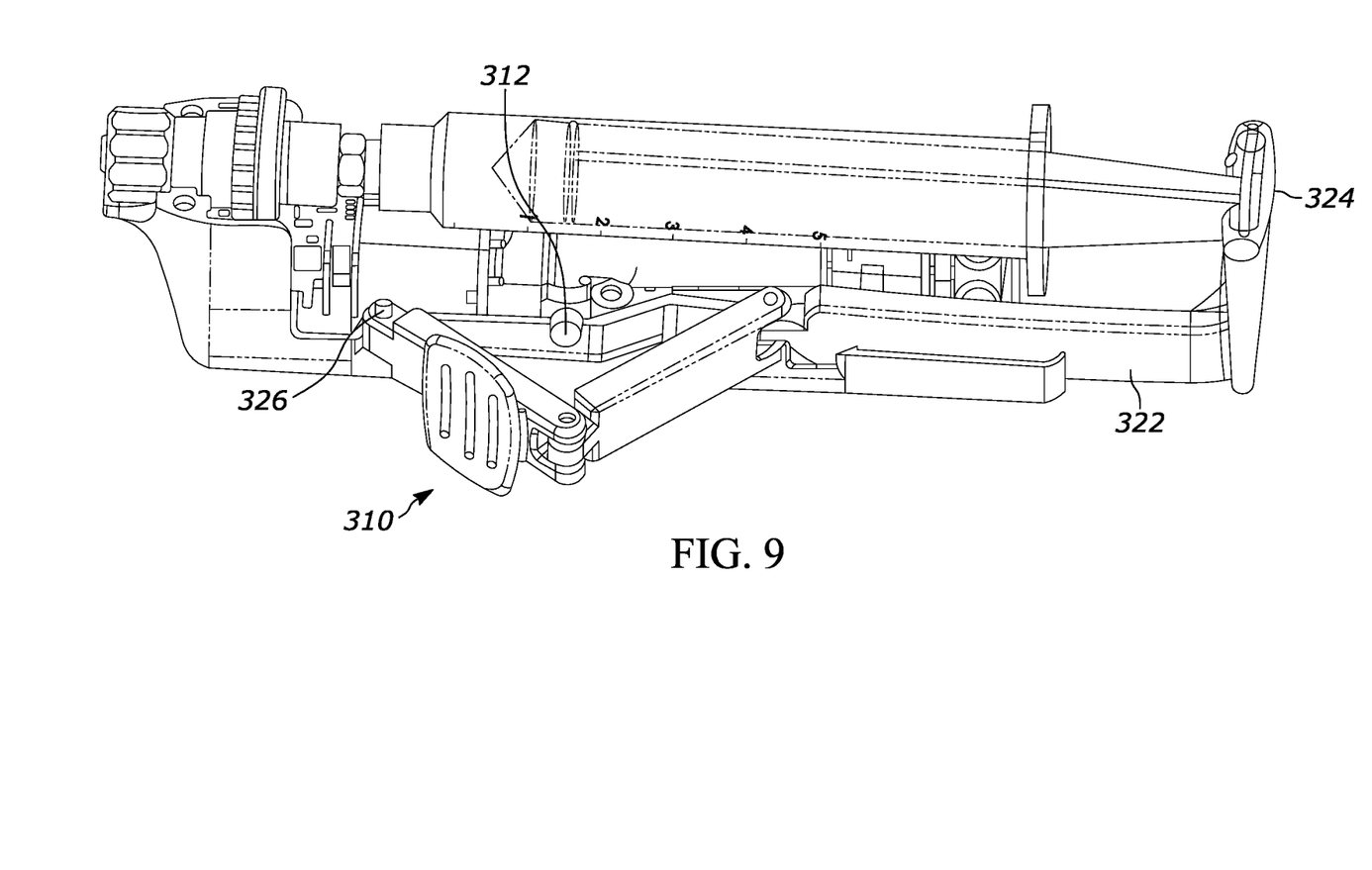
FIG. 9 is a perspective view of the scissor linkage and syringe of FIG. 7 with portions removed to reveal internal components.
Figure 10:
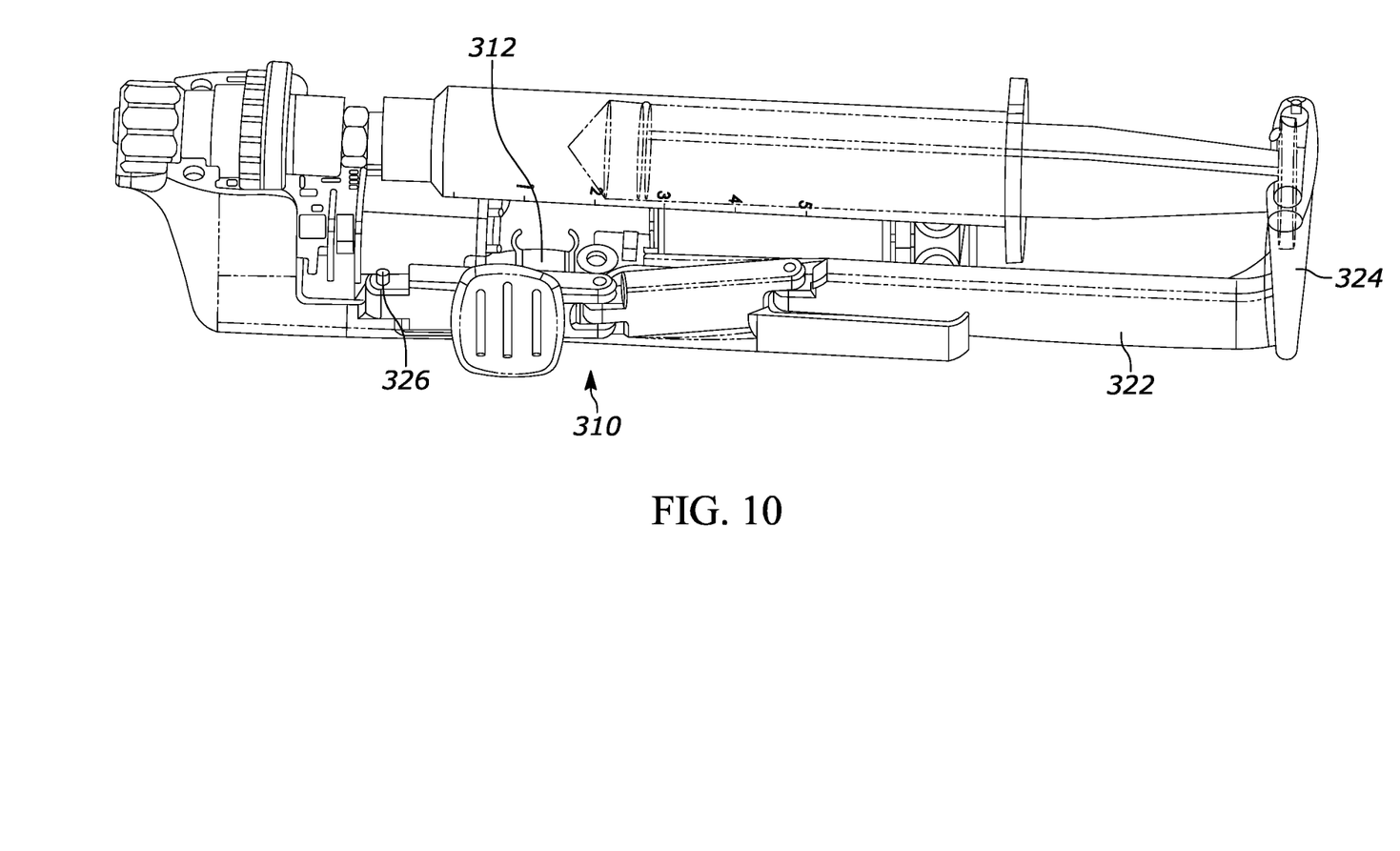
FIG. 10 is a perspective view of the assembly of FIG. 7 in the fully retracted (collapsed) configuration.
Figure 11:
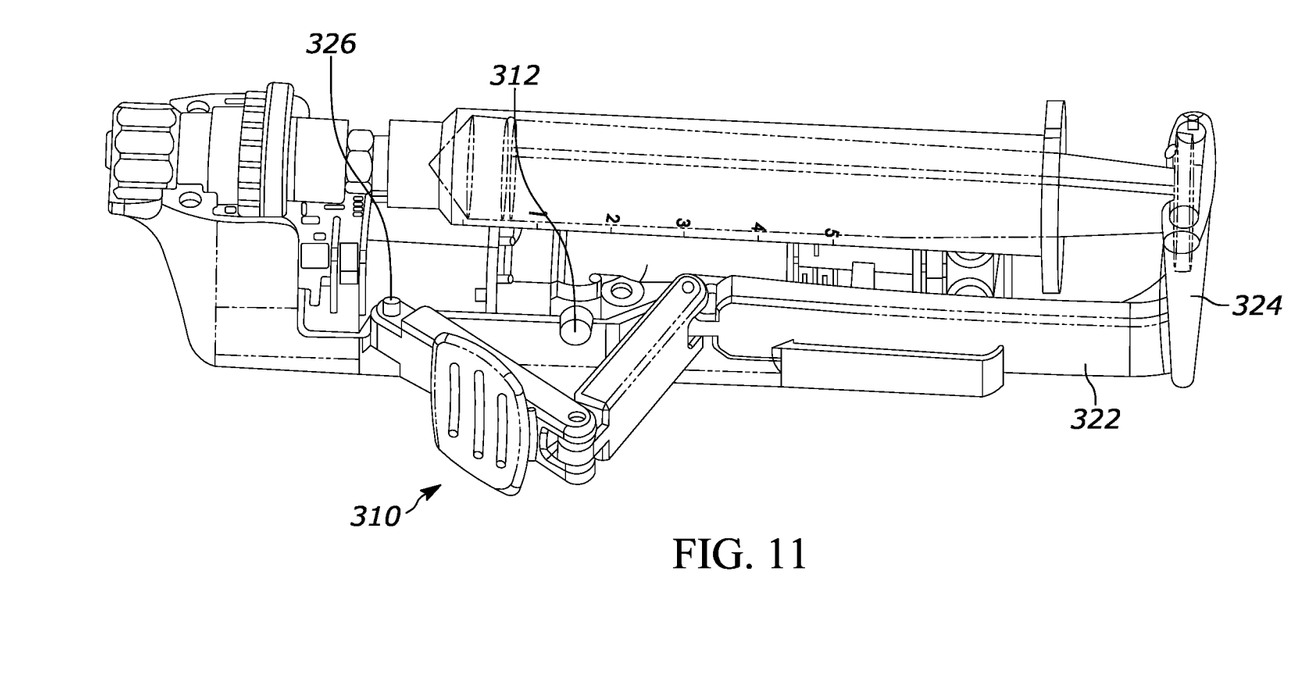
FIG. 11 is a perspective view of the assembly of FIG. 7 in the fully inserted configuration.

A linkage 310 is coupled to the housing 306 and is movable between a first configuration illustrated in FIG. 11, in which the linkage is V-shaped and is distanced from a motor switch 312 to deactivate the motor, through intermediate configurations shown in FIGS. 7-9, to a second configuration shown in FIG. 10, in which the linkage 310 is substantially straight and urges inwardly against the motor switch 312 to energize the motor.

The linkage 310, as best shown in FIG. 8, includes proximal and distal segments 314, 316 rotatably coupled together at a link hinge 318 located between the segments 314, 316. The proximal end of the proximal segment 314 is rotatably coupled at a plunger activation hinge 320 to an elongated plunger activation arm 322 which is oriented parallel to the axis of the syringe 300. The plunger activation arm 322 is attached to or made integrally with a plunger flange receptacle 324 at its proximal end as shown which, like the embodiment in FIGS. 3-6, holds the proximal flange of the plunger. The linkage 310 can both hinge and move translationally along the axis of the syringe 300.

On the other hand, the distal end of the distal segment 316 of the linkage 310 is rotatably coupled to the plunger activation arm by a distal pivot pin 326 (FIGS. 8-11) that permits rotation motion of the linkage 310 relative to the plunger activation arm 322 but which holds the distal end of the distal segment 316 translationally stationary with respect to the plunger activation arm 322. FIG. 8 also shows a control board 328 for causing the motor, shown at 330 in FIG. 8, to oscillate.

With the above structure in mind, instead of a thumb pulling the syringe proximally as for the embodiment in FIGS. 3-6, in the embodiment of FIGS. 7-11 the plunger 304 is retracted by squeezing the linkage 310 against the housing 308 with the assembly being held between thumb and forefinger similar to holding a pencil in either the left or right hand. Initially, using the squeezing motion, the plunger 304 is manually pulled back to the configuration shown in FIG. 9 to leave a predetermined volume in the barrel distal to the distal end of the plunger (such as, e.g., 2 cc). The needle is then inserted into the tissue for harvest. Further squeezing motion retracts the plunger 304 proximally in the barrel 302 while flattening the linkage 310 against the motor switch 312, activating the motor 330 during maximum vacuum in the barrel 302 shown in FIG. 10. The spinning needle serves to harvest tissue. Release of the squeeze pressure allows the vacuum inside the syringe to move the plunger 304 distally in the barrel to the position shown in FIG. 9, with about one cc volume in the barrel 302 distal to the distal end of the plunger 304. This releases the motor switch 312 and deenergizes the motor 330. After the needle is removed from the patient, contents can be expelled onto the slide manually by urging on the receptacle 324 to advance the plunger 304 fully into the barrel 302.

With the above in mind, a medical professional can use either of the embodiments shown in FIGS. 3-11 to retract a syringe plunger proximally relative to a barrel of the syringe to a first proximal position, advance a needle in fluid communication with the barrel of the syringe into an object to be sampled, and energize a motor coupled to the needle to rotate the needle before or after advancing the needle into the patient. As will be discussed further below, the direction of rotation of the motor is reversed to reverse the direction of rotation of the needle during harvesting. Also, the plunger can be retracted to a second position to cause portions of the object to be sucked into the needle as the needle rotates. The direction of rotation of the motor can alternate such that the needle oscillates. The motor is deenergized, the plunger released from the second position and the needle withdrawn from the object, and the plunger advanced distally to expel the portions of the object from the needle onto, e.g., an analysis slide.

Figure 12:
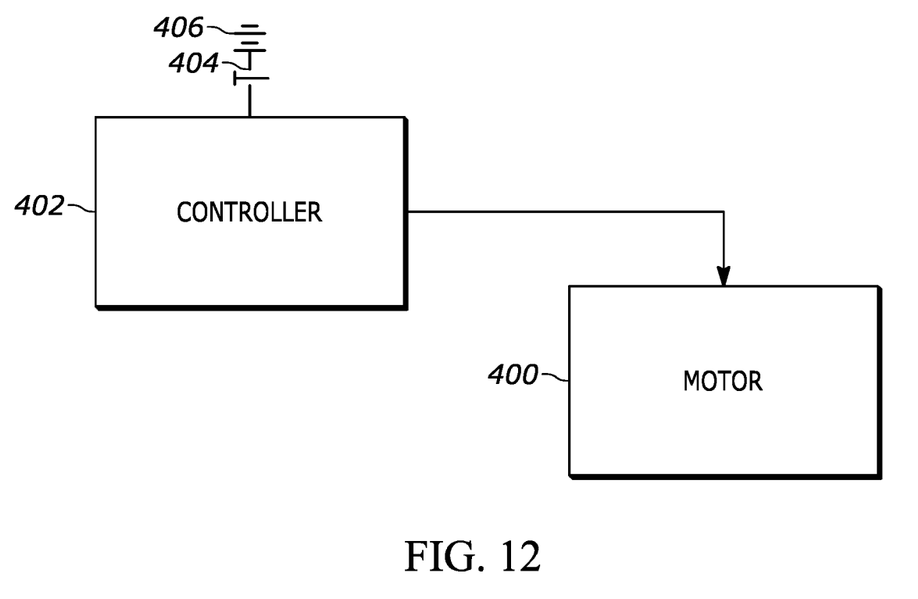
FIG. 12 is a block diagram of a first motor control circuit in which oscillation of the motor is effected by timing.

Now referring to FIG. 12, a motor 400 such as any of the motors described herein is electrically coupled to a controller 402. A motor switch 404 such as any of the motor switches described herein can be operated according to principles discussed above to electrically couple the controller 402 to one or more batteries 406.

Figure 13:
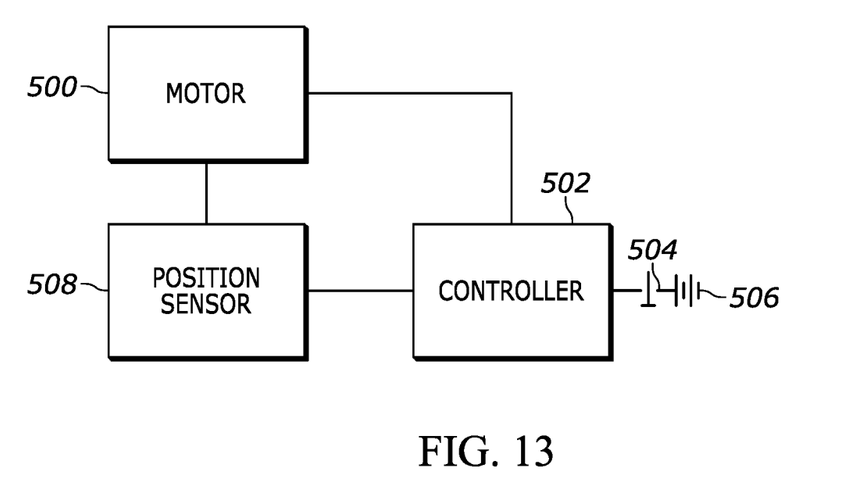
FIG. 13 is a block diagram of a first motor control circuit in which oscillation of the motor is effected by a motor position sensor.

FIG. 13 illustrates an alternate embodiment in which a motor 500 such as any of the motors described herein is electrically coupled to a controller 502. A motor switch 504 such as any of the motor switches described herein can be operated according to principles discussed above to electrically couple the controller 502 to one or more batteries 506. A position sensor 508 such as but not limited to a Hall sensor outputs a signal representative of an angular position of the rotor of the motor 500 and sends the signal to the controller 502.

Figure 14:
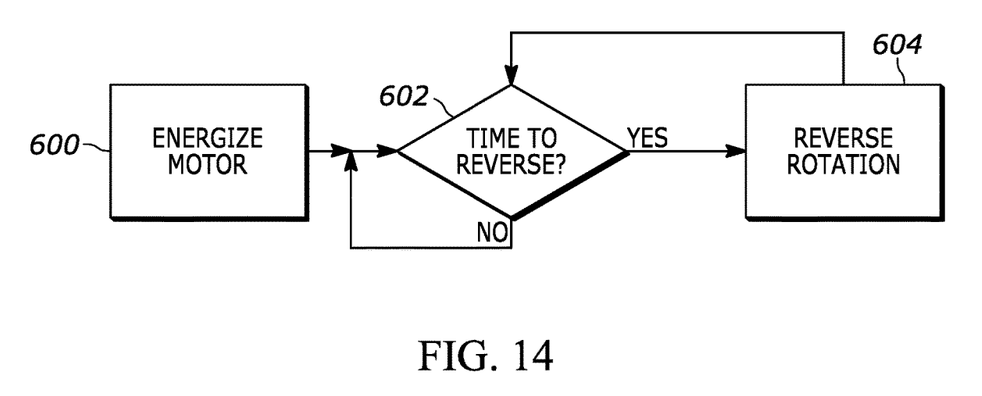
FIG. 14 is allow chart of logic implemented by the circuit of FIG. 12.
Figure 15:
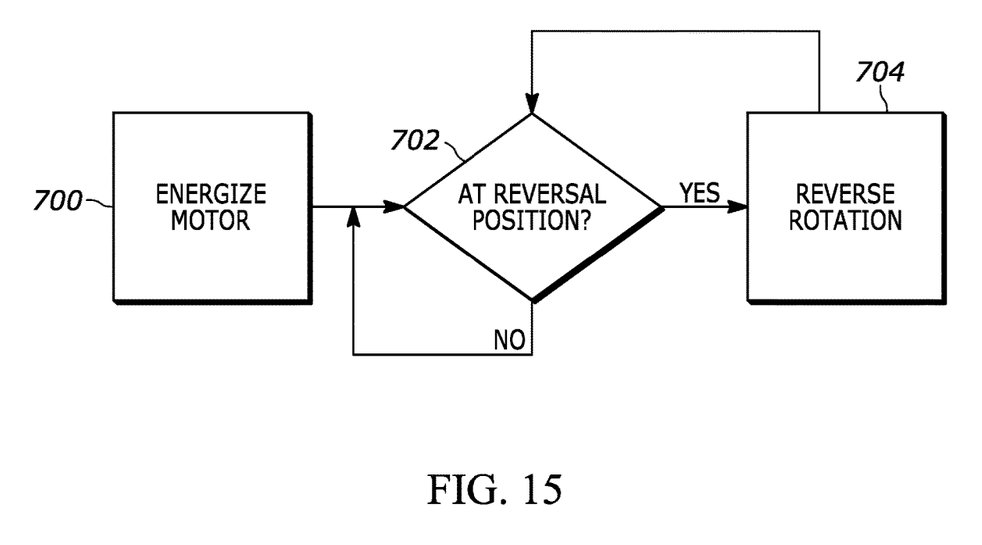
FIG. 15 is a flow chart of logic implemented by the circuit of FIG. 13.

FIG. 14 illustrates logic embodied in the controller 402 of FIG. 11 while FIG. 15 illustrates logic embodied in the controller 502 in FIG. 12. Commencing at state 600, the motor is energized. When a time period is determined to have elapsed at state 602, the direction of rotation of the rotor of the motor is reversed at state 604. The logic loops back to state 602 to continue to reverse the direction of rotation at various time periods, which may be predetermined in some embodiments, until the motor is deenergized, to cause the motor to oscillate during energization.

When a position sensor 508 is implemented as shown in FIG. 13, the logic of FIG. 15 may be employed by the controller. The motor is energized at block 700, and upon determination at state 702 based on the signal from the position sensor that a position of the motor has been attained, the direction of rotation of the motor is reversed at state 704. Note that the position at which rotation is reversed may be multiples of a particular angle so that the motor is reversed after one or multiple rotations. For example, the rotor position for reversal may be at 0 degrees, 720 degrees (two full rotations), then again at 1440 degrees 9 after another two full rotations), etc. Or, the rotor position for reversal may be every 180 degrees, i.e., less than a complete rotor rotation. The logic loops back from state 704 to state 702 to continue to reverse the direction of rotation until the motor is deenergized to cause the motor to oscillate during energization.

While the particular device is herein shown and described in detail, it is to be understood that the subject matter which is encompassed by the present invention is limited only by the claims.

Components included in one embodiment can be used in other embodiments in any appropriate combination. For example, any of the various components described herein and/or depicted in the Figures may be combined, interchanged or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

What is claimed is:

1. A device, comprising:
   a needle having a cutting tip and a hollow interior;
   a syringe coupled to the needle, a tissue chamber being established at least in part by the hollow interior of the needle; and
   a motor coupled to the needle to oscillate the needle back and forth relative to the syringe while the tissue chamber is evacuated to facilitate drawing cells from tissue into the tissue chamber, wherein the syringe comprises a barrel and a plunger slidably disposed in the barrel and movable to evacuate the tissue chamber, and the device further comprises:

a plunger activation assembly comprising a receptacle configured for closely receiving a proximal flange of the plunger, and opposed arms extending distally away from the receptacle, at least one of the arms comprising an inclined ramp that abuts a motor activation switch in a first plunger position to activate the motor and that does not abut the motor activation switch in a second plunger position to deactivate the motor.

2. The device of claim 1, wherein the plunger activation assembly comprises:

a thumb ring extending proximally away from the receptacle.

3. The device of claim 1, comprising a housing supporting the barrel and at least one finger ring extending transversely away from the barrel.

4. The device of claim 1, wherein at least one of the arms is formed with at least one notch, and the device comprises:

a detent arm extending generally parallel to the plunger and comprising a detent adjacent a free end of the detent arm, the detent arm being biased to a first position, in which the detent engages the notch, the detent arm being movable to a second position, in which the detent does not engage the notch.

5. The device of claim 4, wherein the detent is movable to the second position by a detent button.

6. A device, comprising:

a needle having a cutting tip and a hollow interior;

a syringe coupled to the needle, a tissue chamber being established at least in part by the hollow interior of the needle; and a motor coupled to the needle to oscillate the needle back and forth while the tissue chamber is evacuated to facilitate drawing cells from tissue into the tissue chamber, wherein the syringe comprises a barrel and a plunger slidably disposed in the barrel and movable to evacuate the tissue chamber, and the device further comprises:

a housing supporting the barrel;

a linkage coupled to the housing and movable between a first configuration, in which the linkage is V-shaped and distanced from a motor switch to deactivate the motor, and second configuration, in which the linkage is substantially straight and engages the motor switch to energize the motor.

7. The device of claim 6, comprising:

a plunger activation assembly comprising a receptacle configured for closely receiving a proximal flange of the plunger, and at least one plunger activation arm extending distally away from the receptacle, the linkage being connected to the plunger activation arm.

8. A device comprising:

a needle;

a motor coupled to the needle to rotate the needle;

a switch to energize the motor;

a barrel in which at least a portion of the needle can reciprocate and a plunger slidably disposed in the barrel and movable to evacuate the barrel;

a plunger activation assembly receiving the plunger, the plunger activation assembly being movable to open and close the switch; and a receptacle configured for closely receiving a proximal flange of the plunger, and opposed arms extending distally away from the receptacle, at least one of the arms comprising an inclined ramp that the switch in a first plunger position to activate the motor and that does not abut the switch in a second plunger position to deactivate the motor.

9. The device of claim 8, wherein the plunger activation assembly comprises:

a thumb ring extending proximally away from the receptacle.

10. The device of claim 8, comprising a housing supporting the barrel and at least one finger ring extending transversely away from the barrel.

11. The device of claim 8, wherein at least one of the arms is formed with at least one notch, and the device comprises:

a detent arm extending generally parallel to the plunger and comprising a detent adjacent a free end of the detent arm, the detent arm being biased to a first position, in which the detent engages the notch, the detent arm being movable to a second position, in which the detent does not engage the notch.

12. The device of claim 11, wherein the detent is movable to the second position by a detent button.

13. A device comprising:

a needle;

a motor coupled to the needle to rotate the needle;

a switch to energize the motor;

a barrel in which at least a portion of the needle can reciprocate and a plunger slidably disposed in the barrel and movable to evacuate the barrel;

a plunger activation assembly receiving the plunger, the plunger activation assembly being movable to open and close the switch, wherein the plunger activation assembly comprises:

a housing supporting the barrel;

a linkage coupled to the housing and movable between a first configuration, in which the linkage is V-shaped and distanced from the switch to deactivate the motor, and second configuration, in which the linkage is substantially straight and engages the switch to energize the motor.

14. The device of claim 13, wherein the plunger activation assembly comprises:

a receptacle configured for closely receiving a proximal flange of the plunger, and at least one plunger activation arm extending distally away from the receptacle, the linkage being connected to the plunger activation arm.

* * * * *